United States Patent [19]
Gifford et al.

[11] Patent Number: 5,546,322
[45] Date of Patent: Aug. 13, 1996

[54] METHOD AND SYSTEM FOR ANALYZING PLASMA DATA

[75] Inventors: George G. Gifford, Poughkeepsie; Brock E. Osborn, Hyde Park, both of N.Y.

[73] Assignee: International Business Machines Corporation, Armonk, N.Y.

[21] Appl. No.: 226,781

[22] Filed: Apr. 12, 1994

[51] Int. Cl.⁶ .................................................. G01N 31/00
[52] U.S. Cl. .................... 364/497; 364/498; 364/571.01; 364/571.08
[58] Field of Search .................................. 364/468, 498, 364/550, 497, 571.01–571.08; 156/626.1, 643, 345; 204/192.33, 192.32; 356/319, 301, 325, 326; 250/281

[56] References Cited

U.S. PATENT DOCUMENTS

| | | | |
|---|---|---|---|
| 4,008,388 | 2/1977 | McLafferty et al. | 364/498 |
| 4,093,991 | 6/1978 | Christie, Jr. et al. | 364/498 |
| 4,267,572 | 5/1981 | Witte | 364/498 |
| 4,365,303 | 12/1982 | Hannah et al. | 364/498 |
| 4,493,745 | 1/1985 | Chen et al. | 156/626.1 |
| 4,620,284 | 10/1986 | Schnell et al. | 364/498 |
| 4,676,868 | 6/1987 | Riley et al. | 156/643 |
| 5,014,217 | 5/1991 | Savage | 364/498 |
| 5,059,522 | 10/1991 | Harder et al. | 437/129 |
| 5,347,460 | 9/1994 | Gifford et al. | 364/468 |

FOREIGN PATENT DOCUMENTS 0153901  1/1985  European Pat. Off. .

OTHER PUBLICATIONS

Osborn, Brock E., "Statistical Modeling in Manufacturing: Adapting a Diagnostic Tool to Real–Time Applications", IBM J. Res. Dev., vol. 37, No. 4, pp. 491–505, Jul. 1993.

Besag. J., "Spacial Interaction and the Statistical Analysis of Lattice Systems", J. Royal Statistical Soc., 35, pp. 192–236, 1974.

Dempster, A. P., Laird, N. M. and Rubin, D. B., "Maximum Likelihood from Incomplete Data via the EM Algorithm", J. Royal Statistical Soc., 39, pp. 1–38, 1976.

Geman, S. and Geman, D., "Stochastic Relaxation, Gibbs Distributions, and the Bayesian Restoration of Images", IEEE Transactions on Pattern Analysis and Machine Intelligence, vol, PAMI-6, No. 6, pp. 721–742, 1984.

Gerander, U., "Tutorial in Pattern Theory", Division of Applied Mathematics, Brown University, Providence, R.I., Ch. 4, pp. 44–49, 1983.

Gerander, U., "Advances in Pattern Theory, The Rietz Lecture 1985", Division of Applied Mathematics, Brown University, pp. 1–45, 1985.

Hosmer, Jr., D. W. and Lemeshow, S., *Applied Logistic Regression*, A Wiley–Interscience Publication, John Wiley & Sons, p. 6, 1989.

Osborn, B., "The Identification and Estimation of Parameters in Patter Theoretical Models", IBM Technical Report (TR 00.3608), IBM Poughkeepsie, N.Y., pp. 1–25, Mar. 1991.

(List continued on next page.)

*Primary Examiner*—James P. Trammell
*Attorney, Agent, or Firm*—Cutter D. Lawrence; Wayne F. Reinke

[57] ABSTRACT

Analysis of plasma data indicative of gaseous species therein, such as Optical Emission Spectroscopy (OES) data, is aided through the interactive use of a computer. OES data may be calibrated by the computer with minimal input from the user regarding a gas the user knows or suspects is present. The computer then assumes the presence of that gas and assigns relative intensity peaks to known wavelengths for that gas, allowing calibration to take place. Selective identification of particular gases from the data is also possible. Used in conjunction with selective identification, a learning function allows the system to improve the accuracy of future gaseous species identification. Certain characteristics of a particular gas over time, such as intensity at a particular wavelength or at all wavelengths, may also be automatically plotted.

39 Claims, 15 Drawing Sheets

OTHER PUBLICATIONS

Pearse, R. W. B. and Gaydon, A. G., *The Identification of Molecular Spectra*, Fourth Edition, Imperial College, London, Chapman and Hall, pp. 217–219, 1976.

Striganov, A. R. and Sventitskii, N. S., *Tables of Spectral Line of Neutral and Ionized Atoms*, Atomic Spectroscopy Laboratory, I. V. Kurchatov Institute of Atomic Energy (Translated from Russian), IFI/Plenum, New York–Washington, pp. ix, x, 141–144 and 328, 1968.

Gifford, G. G., "Applications of Optical Emission Spectroscopy in Plasma Manufacturing Systems", SPIE vol. 1392 Advanced Techniques for INtegrated Circuit Processing, pp. 454–465, 1990.

METHOD AND SYSTEM FOR ANALYZING PLASMA DATA

BACKGROUND OF THE INVENTION

1. Technical Field

The present invention generally relates to automated data analysis. More particularly, the present invention relates to automated analysis of sensed data representative of gaseous species present in a plasma.

2. Background Art

For most plasma processes, data obtained regarding the gaseous species present in the plasma at any given time must be analyzed off line by an analyst trained to analyze such data. The off-line analysis of such data is important for plasma process control, among other things. However, the analysis of such data has proven to be a difficult and time-consuming process for such analysts.

Certain techniques have been demonstrated as potential monitors of gaseous species in a plasma process. These techniques include Optical Emission Spectroscopy (OES), Fourier Transform Infra-red Spectroscopy, and Laser Induced Fluorescence. Each technique offers unique information about a plasma environment. However, each of these analytical approaches characterizes gaseous species by determining an intensity for one or more electromagnetic wavelengths occurring at the same point in time within the plasma environment.

In the preferred embodiment described herein, an optical emission spectrometer is utilized as the sensor of choice. An optical emission spectrometer is a commercially available device used to detect the presence and relative concentrations of various gases in a plasma chamber. The optical emission spectrometer works by detecting light emitted from within the chamber, both the relative intensity thereof and the corresponding wavelength.

The process of analyzing data relating to the gaseous species in a plasma is historically a manual one. However, in recent years limited progress has been made with respect to partially automating the analysis. For example, some automated systems hold known intensity and wavelength data for particular gases and assist in manual calibration of the raw data. None of the existing systems have fully utilized the available computer technology to speed the analysis and increase the accuracy of the results.

Thus, a need exists for more extensive automated assistance in interpreting data obtained from a plasma process regarding gaseous species therein.

SUMMARY OF THE INVENTION

Briefly, the present invention satisfies the need for improved automated data analysis for plasma-related data by providing automatic calibration with minimal analyst input, selective automatic identification of one or more gaseous species, automatic analysis of gaseous species in a plasma over time and a learning function to improve the automatic identification of gaseous species in a plasma.

One object of the present invention is to provide automated assistance in the interpretation of data relating to gaseous species obtained from a plasma process.

Another object of the present invention is to provide automated calibration of data relating to gaseous species in a plasma with limited input from an analyst.

A further object of the present invention is to provide automated assistance that improves accuracy over time in the interpretation of data relating to gaseous species in a plasma.

Still another object of the present invention is to provide selective automated identification of gaseous species in a plasma from data obtained regarding the plasma.

Further, it is an object of the present invention to provide automated assistance in analyzing the changes in gaseous species in a plasma process over time from data obtained regarding the plasma.

In accordance with the above objects, the present invention provides in a first aspect a method for analyzing data derived from a plasma comprising a plurality of gaseous species. The method comprises the steps of inputting the data into a computer, inputting information regarding the plasma into the computer, automatically calibrating via the computer the data, and identifying one of the plurality of gaseous species. The date inputted to the computer is derived from electro-optical signals generated in a plasma process and thereafter sensed. The method may include selecting at least one gaseous species to be identified, where the identifying step comprises identifying the at least one gaseous species. Identifying the at least one gaseous species may be done based on assumed parameters; if so, the parameters may be modified based on the results of the identifying step such that a subsequent identification is improved.

In a second aspect of the present invention, an exemplary system is provided implementing the principles of the method of the first aspect.

These, and other objects, features and advantages of this invention will become apparent from the following detailed description of the various aspects of the invention taken in conjunction with the accompanying drawings.

DETAILED DESCRIPTION OF THE INVENTION

This discussion requires an examination of certain methods of statistical analysis used for interpreting data from an optical emission spectrometer. Such an examination can be found in an article by Brock E. Osborn, entitled "Statistical Modeling in Manufacturing: Adapting a Diagnostic Tool to Real-Time Applications," IBM J. Res. Develop., Vol. 37 No. 4, July 1993 (hereinafter, "the Osborn article"), which is hereby incorporated herein by reference in its entirety.

An optical emission spectrometer is preferably employed herein for the detection of the presence and relative concentration of gases in a processing chamber. Assuming familiarity with the Osborn article, the present invention will be described in an exemplary form of interactive graphically oriented system. The discussion presented herein is provided by way of example only and those skilled in the art will recognize that various modifications and substitutions to the structures and methods described can be made without departing from the scope of the present invention as defined by the claims appended hereto.

As noted initially, an optical emission spectrometer (hereinafter, "spectrometer") works by detecting the light that is emitted from electron transitions occurring within atoms and molecules, and particularly, gaseous or vaporized atoms and molecules. Spectrometers are used to characterize the chemistry of the plasma environment during wafer manufacturing in order to ensure process reproducibility and quality. Further details of optical emission spectroscopy are provided in an article by G. Gifford, entitled "Applications of Optical Emissions Spectroscopy in Plasma Manufacturing Systems", SPIE Microelectronic Integrated Processing Symposium (1990).

Figure 1:
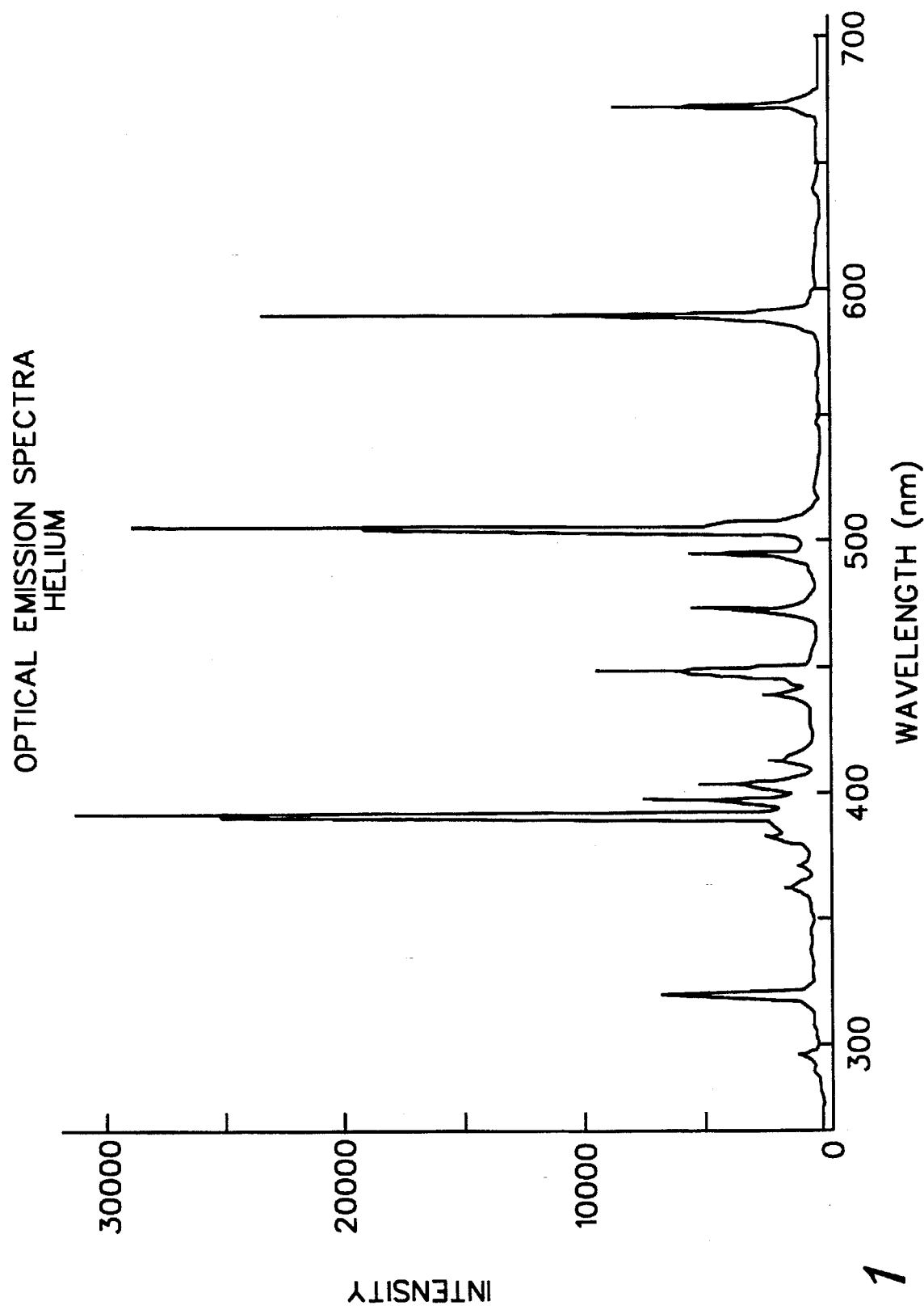
FIG. 1 is a hand drawn representation of a graph of an optical emission spectra for helium.

A hand drawn example of an optical emission spectra for helium is shown in FIG. 1, which is simply a graph of intensity of energy emissions versus measured wavelengths.

A spectrometer measures light emission at specific wavelengths. Adjacent wavelengths can be acquired through either a series of multiple diodes, e.g. 512 or 1024 diodes, or a single diode where light of multiple adjacent wavelengths is sequentially exposed to a single detector or diode as with a scanning monochromator. Hence, an important characterization of spectrometer devices is their level of wavelength resolution. FIG. 1 is an example of low resolution spectrometer data where readings are taken at approximately every 0.6 nm. Spectrometer devices can measure at much finer resolutions, but this requires a longer time to cover the same range of wavelengths, which eventually limits their practical use for real time applications. Readings taken at a resolution lower than 1.0 nms provide a coarse spectrum that makes species identification difficult for an expert, as well as for an automated routine, at least with current automation technology.

Tables are available in the open literature which indicate where peaks for a particular gas should appear and the approximate relative intensities of these peaks. A portion of such a table for helium is reproduced in Table 1 (See J. Reader and C. Corliss, "Line Spectra of the Elements", CRC Handbook of Chemistry and Physics (1983)).

TABLE 1

| Sample OES Peaks for Helium | |
|---|---|
| Wavelength (nm) | Relative Intensity |
| 388.865 | 500 |
| 396.4729 | 20 |
| 402.6191 | 50 |
| 447.1479 | 200 |
| 501.5678 | 100 |
| 587.562 | 500 |
| 587.597 | 100 |
| 667.815 | 100 |

The statistical problem presented is to identify the gases that are present in the chamber at a particular point in time given measured OES data. The first step is to determine the wavelengths at which the peaks appear in the graph. Peak identification can be accomplished in a number of different ways, as one skilled in the art will know, one of which will now be described.

The OES data can be thought of as consisting of a set of ordered pairs, $\Gamma_i = (\lambda_i, I_i)$, where $\lambda$ is the wavelength and $I$ is the corresponding intensity level at that wavelength. The graph in FIG. 1 consists of 700 points (i.e., "i" ranges from 1 to 700), with $\Gamma_i$ being provided at about every 0.6 nm.

First, the $\Gamma_i$ are reordered so that they are in descending order of intensity, i.e.: $I_1 \geq I_2 \geq \ldots \geq I_N$. Next, the $\Gamma_i$'s are grouped together in the following manner:

1. Start the first group with $\Gamma_1$;
2. Set "i"=2;
3. If $\lambda_i$ is one greater or one less than one of the $\lambda$'s in any existing group, then put $\Gamma_i$ into that (or those) groups(s) (Otherwise, create a new group starting with $\Gamma_i$);
4. Set "i"="i"+1; and
5. If "i"≦N then go to 3 above. (Otherwise, stop.)

Once this process is complete, K groups will be defined corresponding to the K peaks in the graph. The wavelength and intensity of each peak is given by the $\Gamma_i$ that started each group. Note that the peaks (if they exist) at the end points of the graph (i.e., the smallest and largest wavelengths) should be disregarded because data is typically truncated at those points.

The above-outlined procedure for identifying the wavelength of each peak in a graph is limited by the level of resolution of spectrometer being used. In the case presented, readings were obtained every 0.6 nm, and hence a peak identified to be at, for example, 396.3 nm could actually be somewhere between 396.0 and 396.6 nm. The accuracy of the estimation of the wavelength can be improved through an extrapolation procedure which is referred to herein as peak sharpening.

Figure 2:
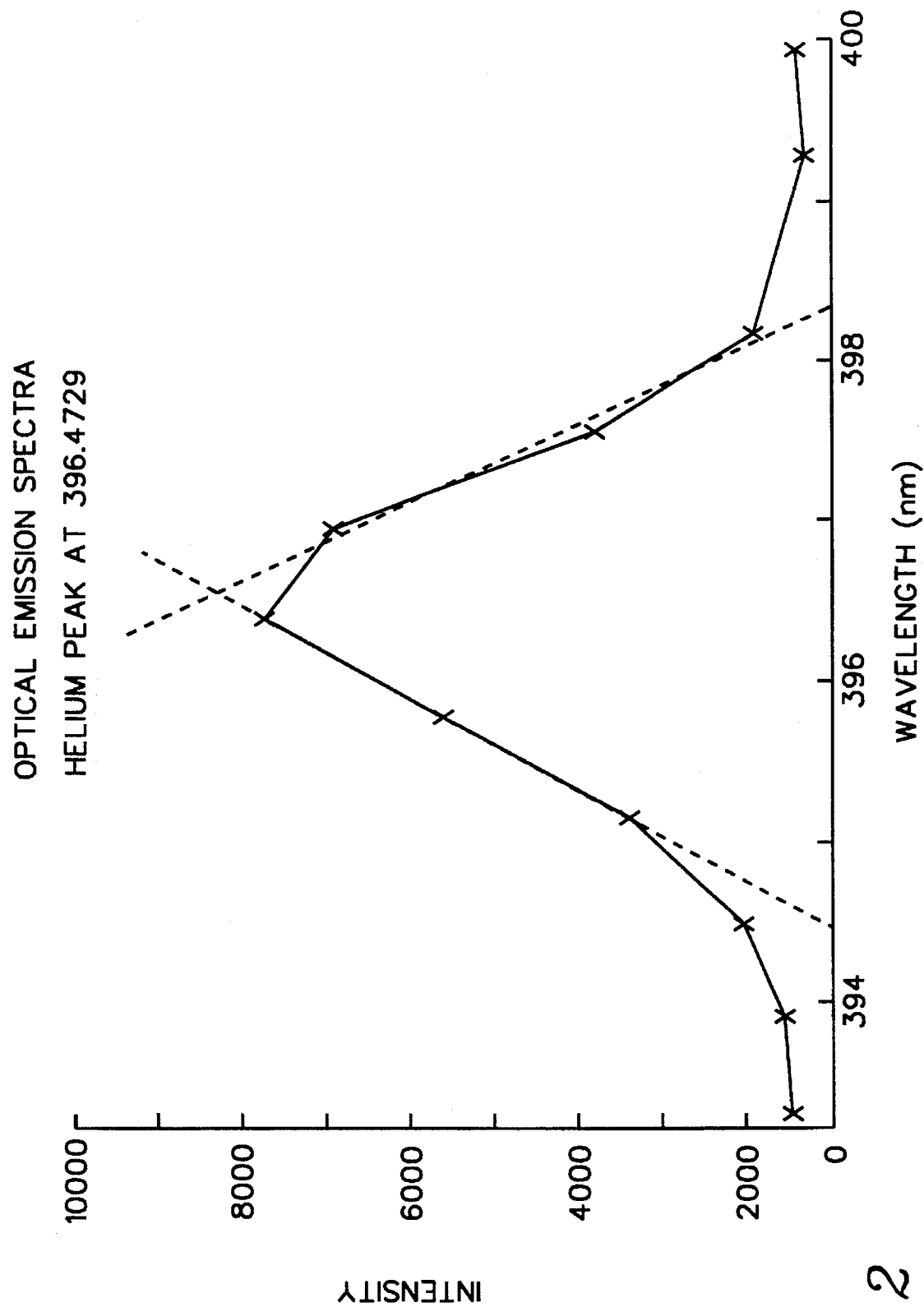
FIG. 2 is a graph of a magnified portion of the optical emission spectra of FIG. 1 useful in explaining "peak sharpening".

FIG. 2 shows an enlargement of a particular peak in the helium plot of FIG. 1. This peak appears at approximately 396.3 nm. Two regression lines (shown as dotted lines) have been fitted thereto using three points on either side of the peak to define a sharpened peak at 396.5 nm, which corresponds more closely to the actual location of the peak (according to Table 1) of 396.4729 nm. If the intensity of the peak had been larger, more points could have been used on either side to increase the accuracy.

Figure 3:
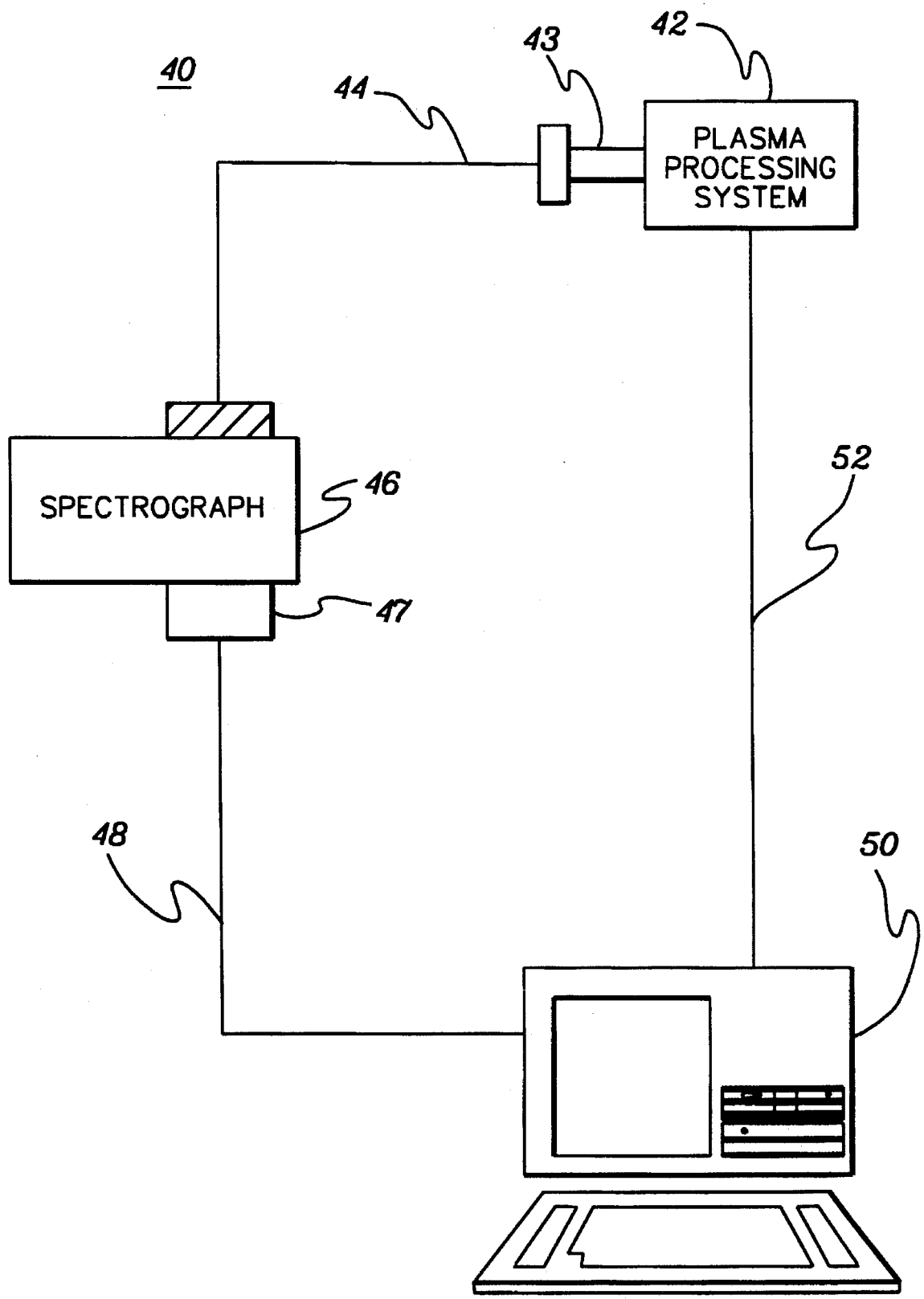
FIG. 3 is a block diagram of an exemplary processing system from which data can be collected and analyzed according to the present invention.

Optical emission spectroscopy (OES) is a sensitive analytical technique that can provide detailed information about the chemical composition and energy states of atoms and small molecules excited by an appropriate energy source. In FIG. 3, a plasma processing system 42 is conventionally used in semiconductor manufacturing for etching and depositing materials having such an energy source. From such a process, data may need to be analyzed off-line for various purposes. Generic plasma processing system 42 is coupled by a fiber optic cable 44 to a generic spectrograph 46. As is well understood in plasma processing, an energy source excites electrons in the gas used for processing the semiconductor. The deexcitation mechanism often produces light as absorbed energy is released by the gas. The wavelengths of this released light are determined by the difference in energy states of the atoms or molecules. Each atomic and molecular species has a unique set of wavelengths at which it emits light. This processing system can have a window 43, through which this light can be monitored.

Coupled to window 43 is fiber optic cable 44. Fiber 44, often made of silica, collects light from system 42 and passes the light to spectrograph 46. The spectrograph diffracts the incoming light to separate the various wavelengths emitted by gas species in plasma processing system 42. The focal length of the spectrograph and the spacing between diffraction rules on the grating determine the effective resolution of the spectrograph and thus the degree of separation of the various wavelengths. At the exit plane of the spectrograph a detector 47 is placed to intercept the diffracted light. This can either be a single channel detector, if the grating will be rotated to pass multiple wavelengths by it, or a multichannel diode array or CCD (2-D array of charged coupled devices). The photodetector produces an electronic signal proportional to the flux of light it receives. If there are multiple channels then multiple electronic signals are produced.

An electrical cable 48 carries the electric signals produced by photodetector 47 to an electronic controller/computer 50 where signals are initially converted from analog form to digital form, which can then be read by the controller/computer 50. This unit controls the time that the photodetector 47 collects each set of signals. The computer is used to run software which instructs the controller and analyzes incoming data. The software that is run on the controller/computer determines the automatic analysis and feedback control capabilities of the monitor/control system.

Figure 4:
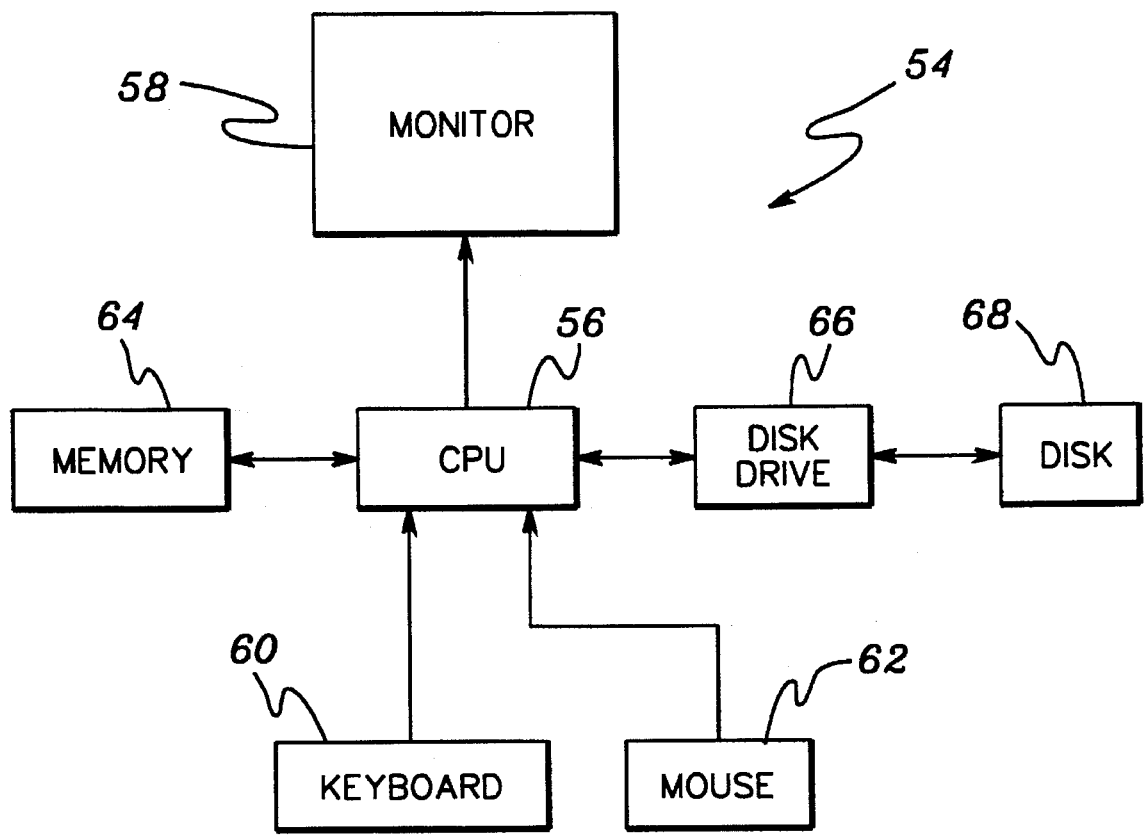
FIG. 4 depicts an exemplary computer system programmed to perform the method of the present invention.

FIG. 4 depicts, in block diagram form, an exemplary computer system 54 properly programmed for practicing the present invention; that is, for providing an interactive tool for interpreting plasma data, such as optical emission spectroscopy (OES) data. Computer system 54 comprises central processing unit 56, monitor 58, keyboard 60, mouse 62, memory 64, disk drive 66 and disk 68. Monitor 58 preferably has an adequate resolution for graphics. It will be understood, however, that such a properly programmed computer could take many forms, such as a main frame or a lap top computer. The operation of computer system 54 will be understood by one skilled in the art, thus, details concerning its operation are omitted. It will also be understood that the hardware facilitating the interactive nature of the invention can manifest itself in any number of ways. For example, function keys could be used by the user, a menu driven software approach could be used, or more elaborate schemes could be used, such as a touch screen, to provide the interactive element. In addition, disk drive 66 and disk 68 (and, in general, magnetic storage retrieval systems) could be replaced by, for example, an optical data storage/retrieval system.

Wavelength and intensity data, such as OES data, derived from a plasma process exists on disk 68 and is input into computer system 54 through disk drive 66 and may be in any of various formats, such as ascii files or compressed binary files. FIGS. 5 through 12 depict an exemplary series of what a user (not shown) may see on monitor 58 when operating computer system 54 to assist in the interpretation of the input wavelength and intensity data.

Figure 5:
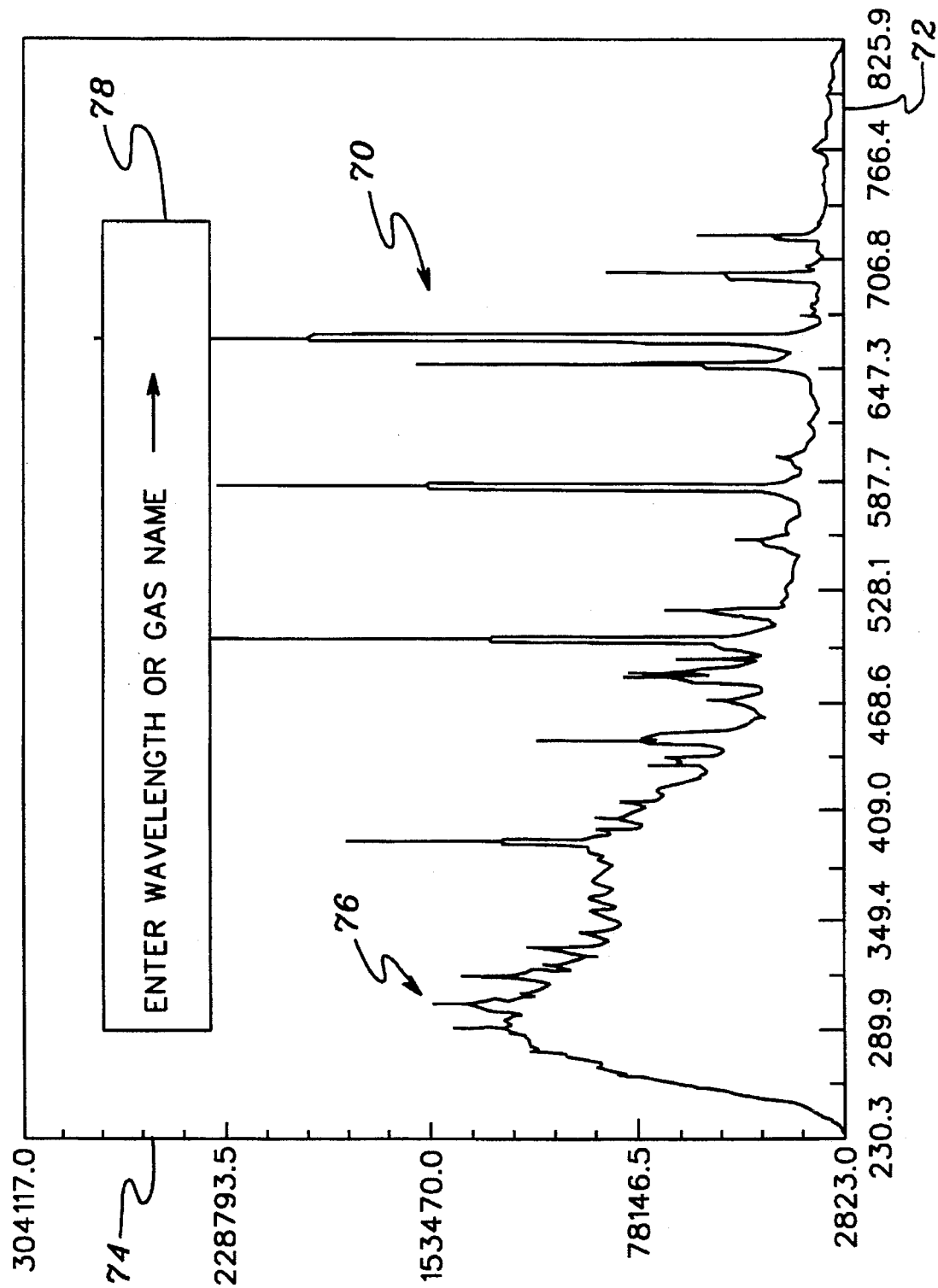
FIG. 5 depicts a plot of uncalibrated OES data with a prompt requesting assistance with manual calibration.

FIG. 5 depicts a plot 70 of uncalibrated or raw OES data obtained from some plasma process, for example, semiconductor fabrication. Plot 70 plots visible light wavelength in nanometers along X axis 72 against relative light intensity on Y axis 74. One goal of plotting the OES data is to identify, via the peaks in plot 70, such as peak 76, the identity of one or more gases in the plasma. This can be done, for example, through the use of the analysis techniques described in the Osborn article (hereinafter, "OES Impurity Analysis" or "OESIA"). However, before the gases can be identified with any reasonable degree of certainty, the OES data must first be calibrated; that is, a proper wavelength scale must be found for the OES wavelength data.

Manual calibration of OES data is a time consuming and difficult process. The burden of calibration can be lessened through the use of a computer, such as system 54. By manually identifying several peaks in plot 70, either by wavelength or by gas, the computer is provided with information assumed to be true and the rest of the data can be made to fit the plot, for example, by employing linear regression. In FIG. 5, system 54 prompts (78) the user to enter either the wavelength of peak 76 or the gas to be assumed associated therewith.

As an alternative to the manual calibration process described above, the present invention allows for automated calibration and requires the user to merely enter the name of a single gas known or believed by the user to have been present in the plasma when the data was obtained. This aspect of the present invention will hereinafter be referred to as "dynamic calibration".

Figure 6:
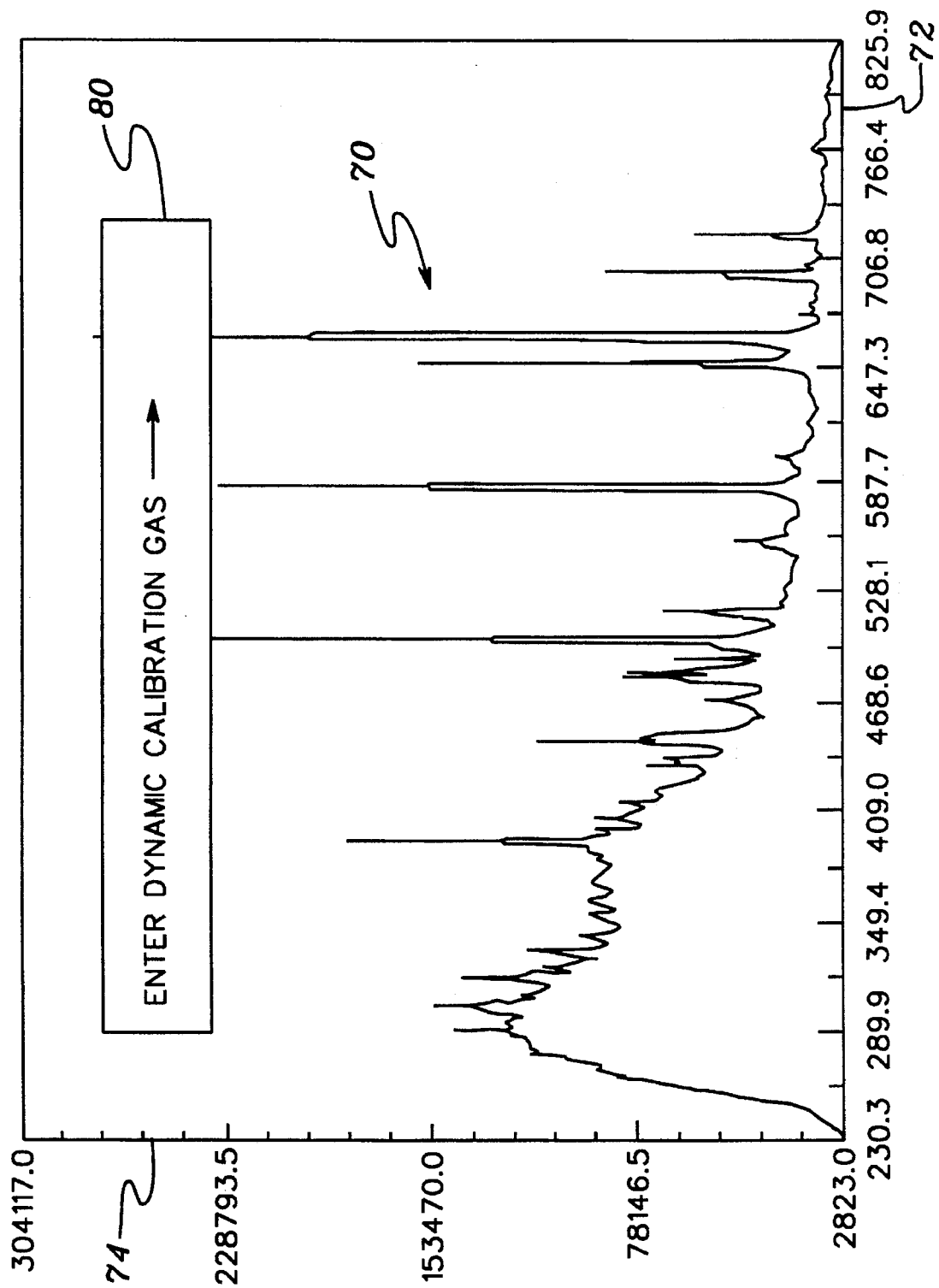
FIG. 6 depicts the plot of FIG. 5 with a prompt requesting entry of a dynamic calibration gas for automatic calibration according to the present invention.

FIG. 6 depicts the plot 70 of FIG. 5 with a prompt 80 from system 54 for the user to identify the dynamic calibration gas to be assumed present in the plasma. Preferably, the identified gas is known to the user to be present in the plasma, based on, for example, the user's knowledge of the particular plasma process, and is the gas having the highest peaks in plot 70. System 54 will identify a predetermined number of the highest peaks, say five, as corresponding to the identified gas. In the simplest implementation, the computer searches for the predetermined number of highest peaks from the data and proceeds from the assumption that they all correspond to the identified gas. However, it will be understood that it need not be the highest peaks nor must the number of peaks be five. The specifics of the dynamic calibration routine will be discussed in detail subsequently. From the information provided by the user, the computer can find the X axis scale providing the best fit for the OES data.

Figure 7:
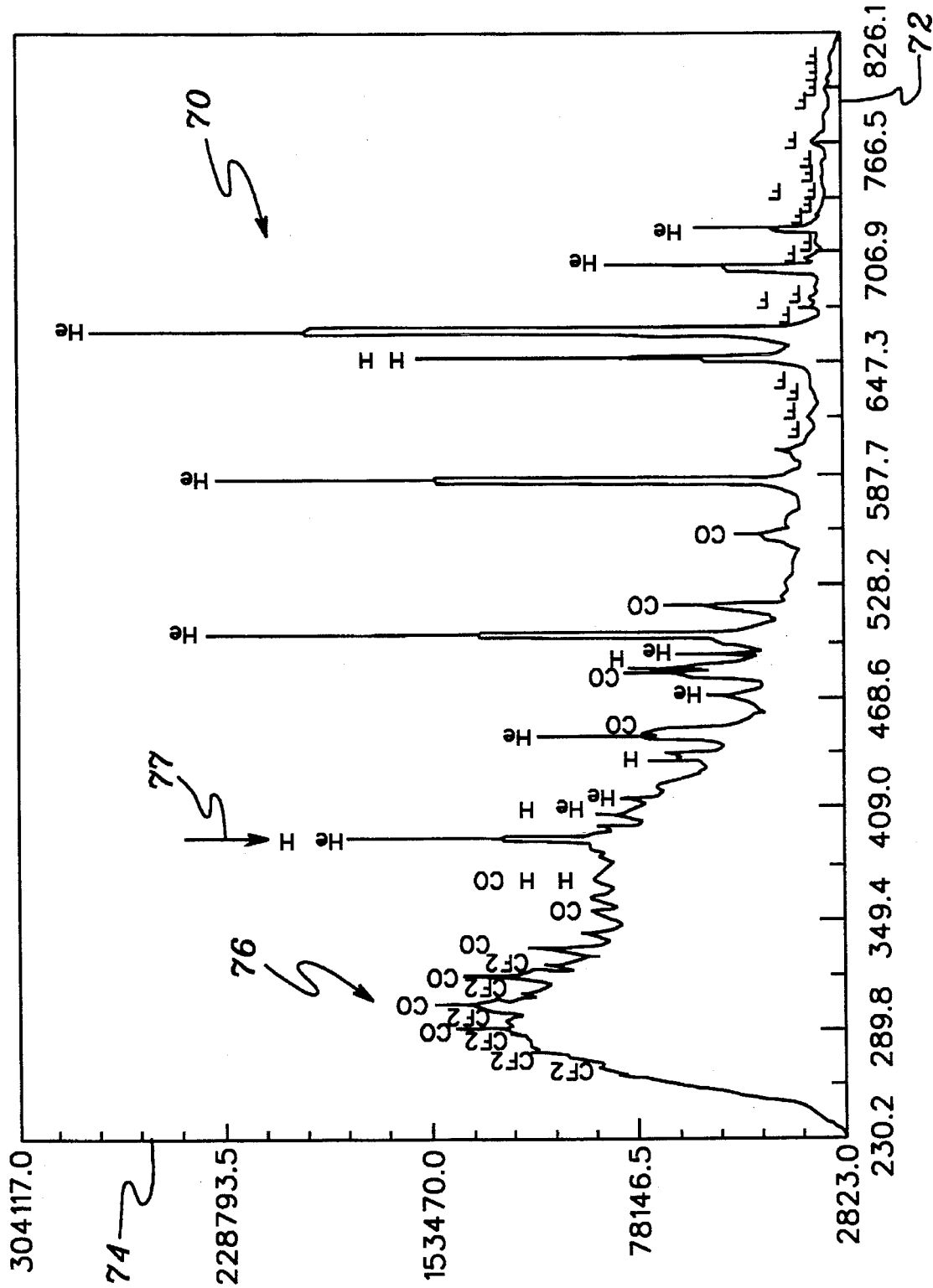
FIG. 7 depicts the plot of FIG. 6 after automatic calibration and after the peaks have been associated with gaseous species.

FIG. 7 depicts plot 70 after the peaks have been identified, in response to an appropriate indication from the user to do so, such as hitting a particular function key. For example, peak 76 has been identified as corresponding to carbon monoxide (CO).

Another feature of the present invention allows the user to indicate to system 54 a particular peak and the computer will provide detailed information not provided by and/or not readily discernable from plot 70. For example, arrow cursor 77 in FIG. 7 can be moved to a particular peak in plot 70, and system 54 would indicate to the user, perhaps through a window such as window 82 in FIG. 8, the actual wavelength for that peak according to the scale of X axis 72. In addition, it may be desirable to include other information, such as the full name of the gas and/or the actual wavelength for that peak according to the available tables, such as Table 1 herein.

Figure 8:
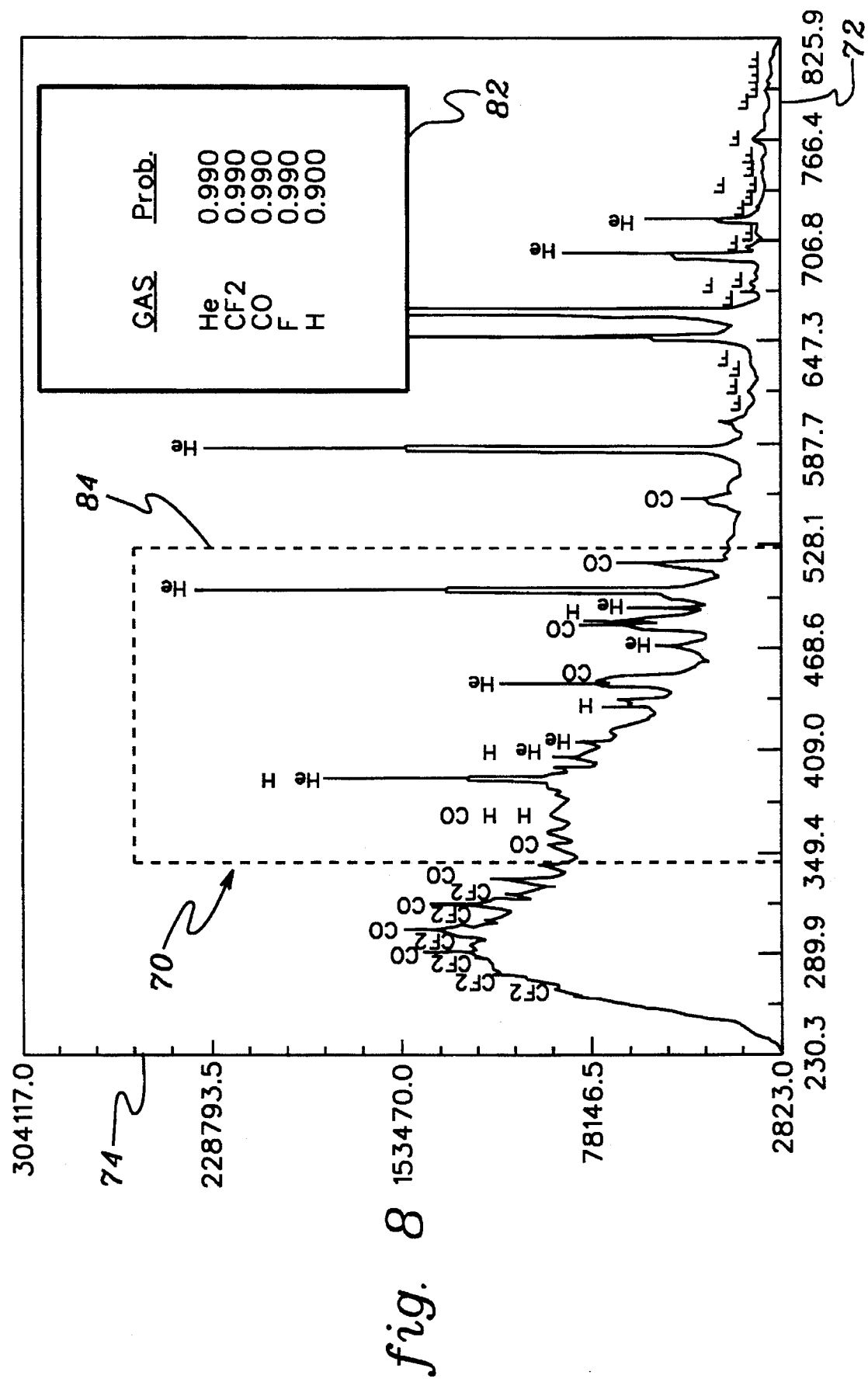
FIG. 8 depicts the plot of FIG. 7 with a window indicating the most likely configuration and a probability for each gas in the most likely configuration.
Figure 9:
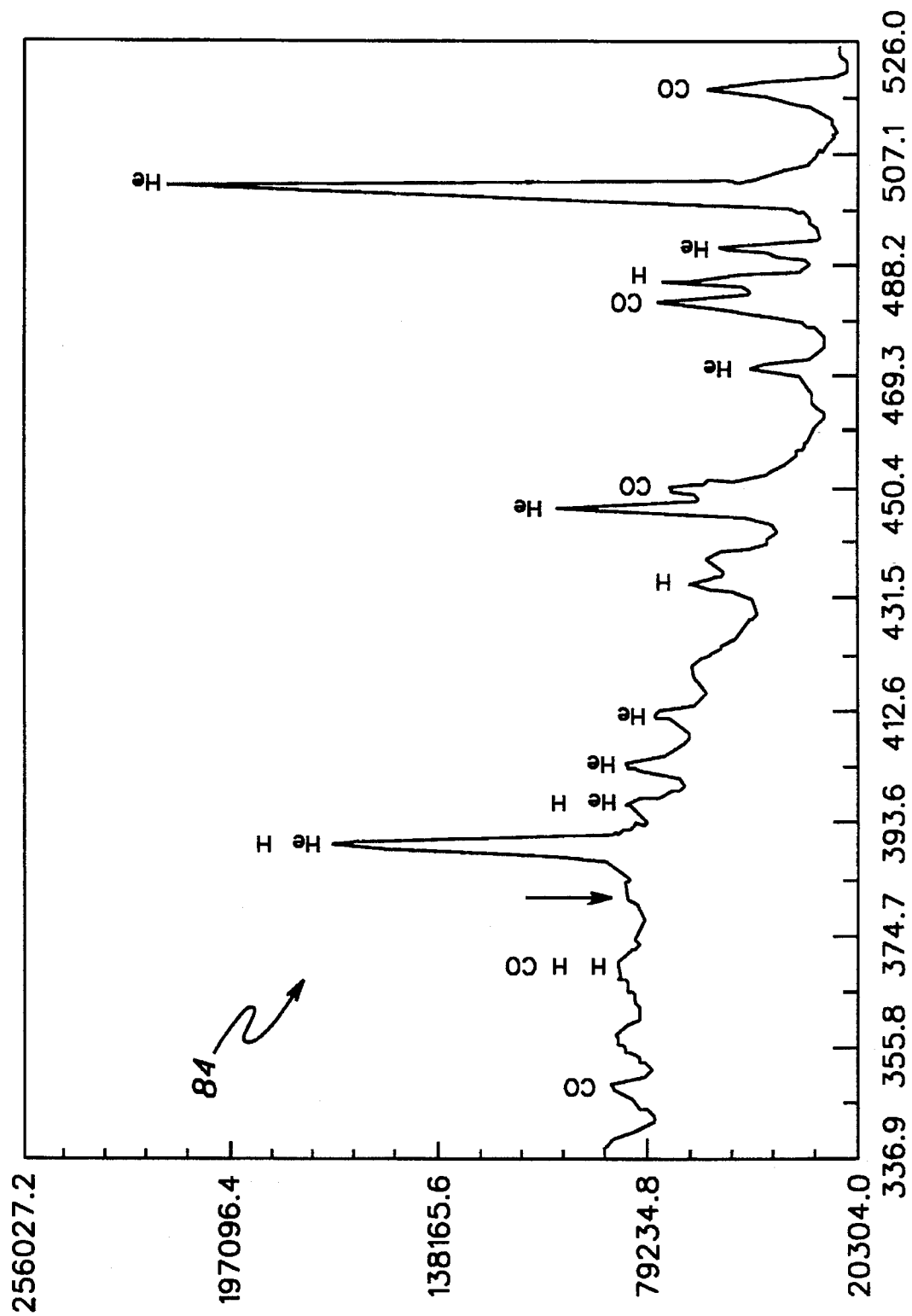
FIG. 9 depicts an exploded view of a portion of the plot of FIG. 7.
Figure 14:
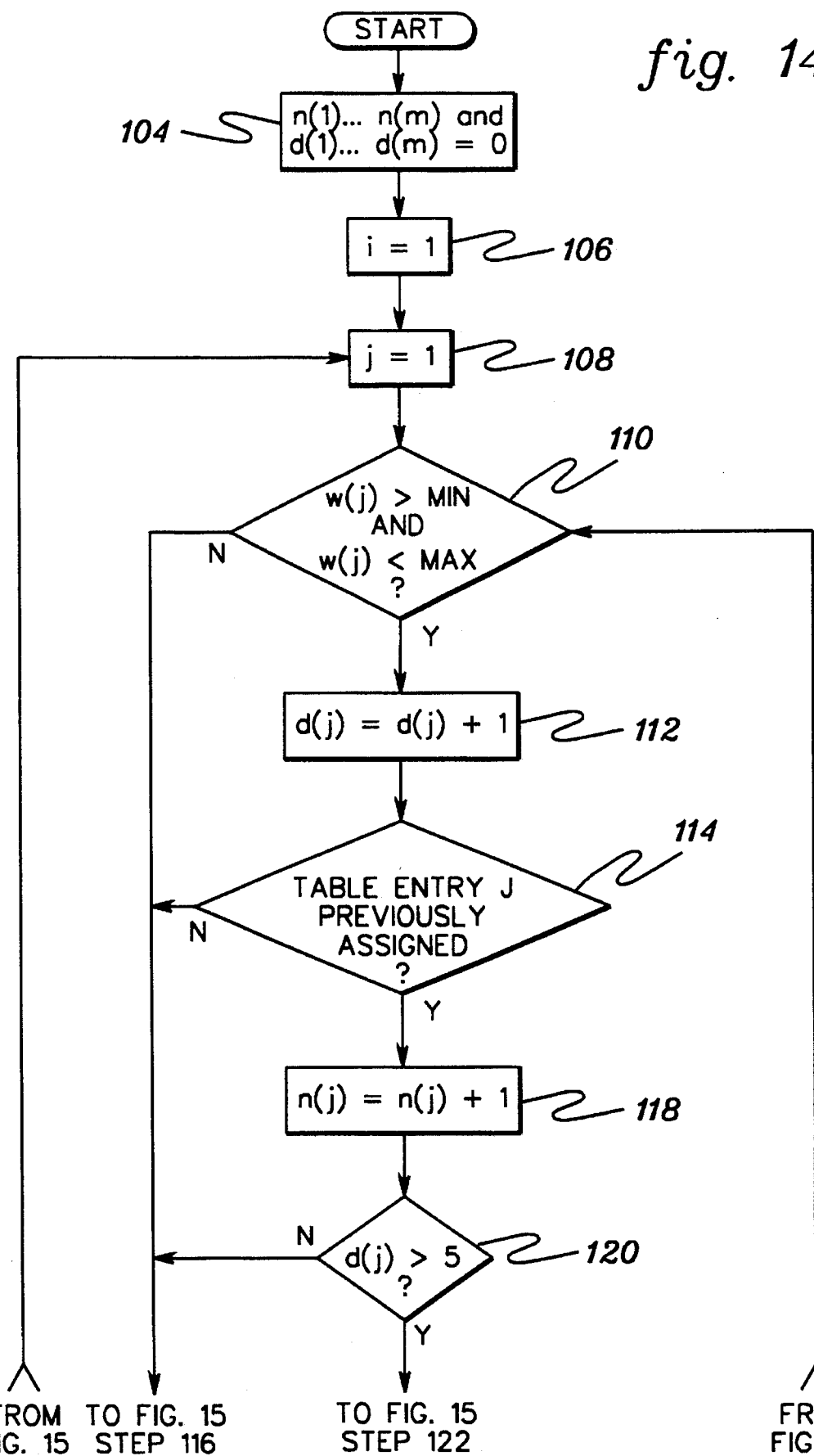
FIGS. 14 and 15 are flow diagrams for the learning routine of the present invention.

FIG. 8 depicts the plot 70 of FIG. 7 with window 82 listing the component gases of the most likely configuration of the gases in the plasma and a probability for each that it is actually present in the plasma, based on the OES data. Window 82 appears in response to an appropriate action taken by the user, for example, pressing a function key. FIG. 9 depicts an exploded view of a portion 84 of plot 70 in FIG. 8 after the X axis 24 has been narrowed. As can be seen in FIG. 14, an exploded view allows the user to see more detail in particular areas of plot 70, such as crowded areas.

Figure 10:
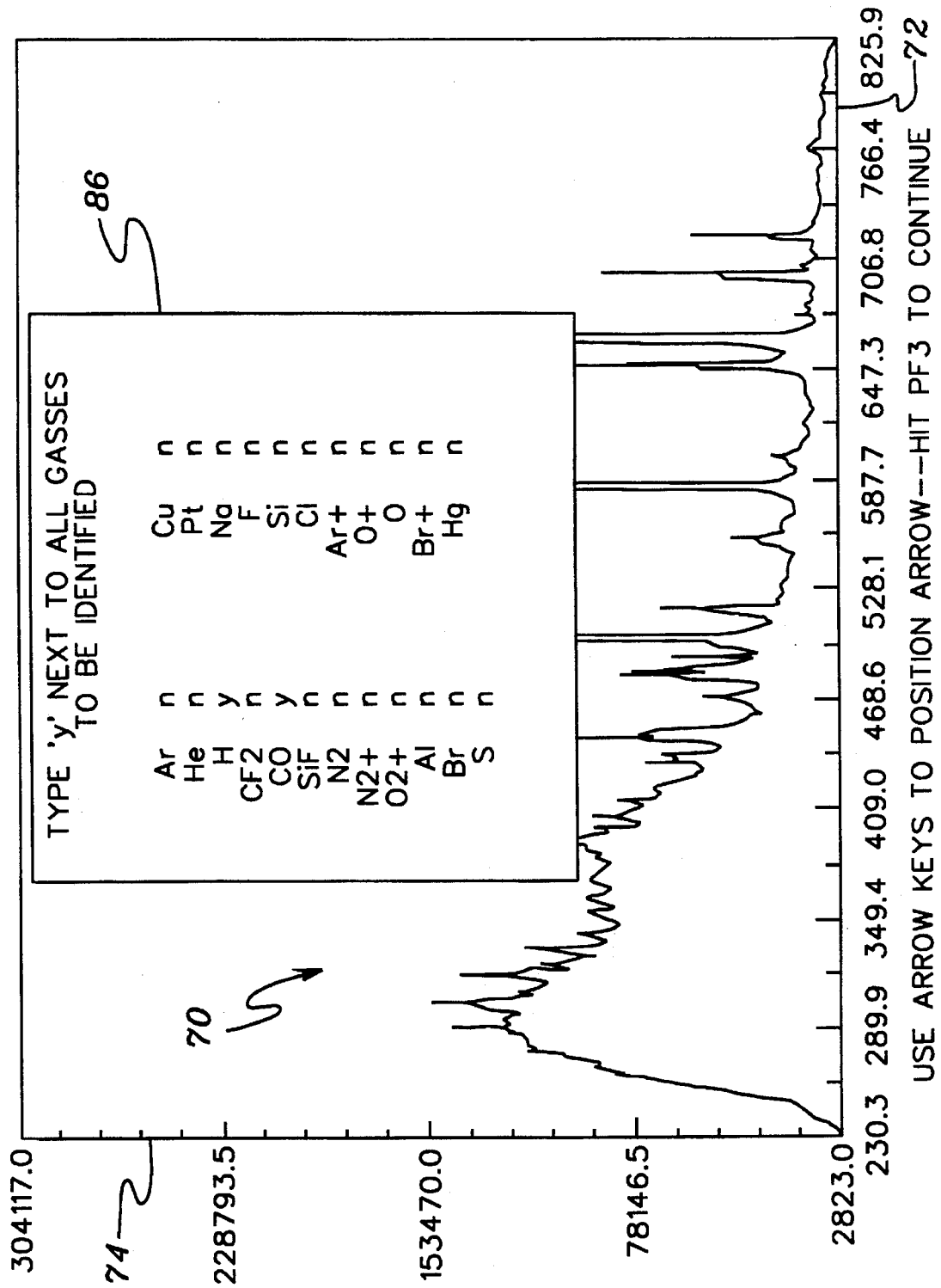
FIG. 10 depicts the plot of FIG. 6 with a prompt requesting an indication of all gases for selective identification according to the present invention.
Figure 11:
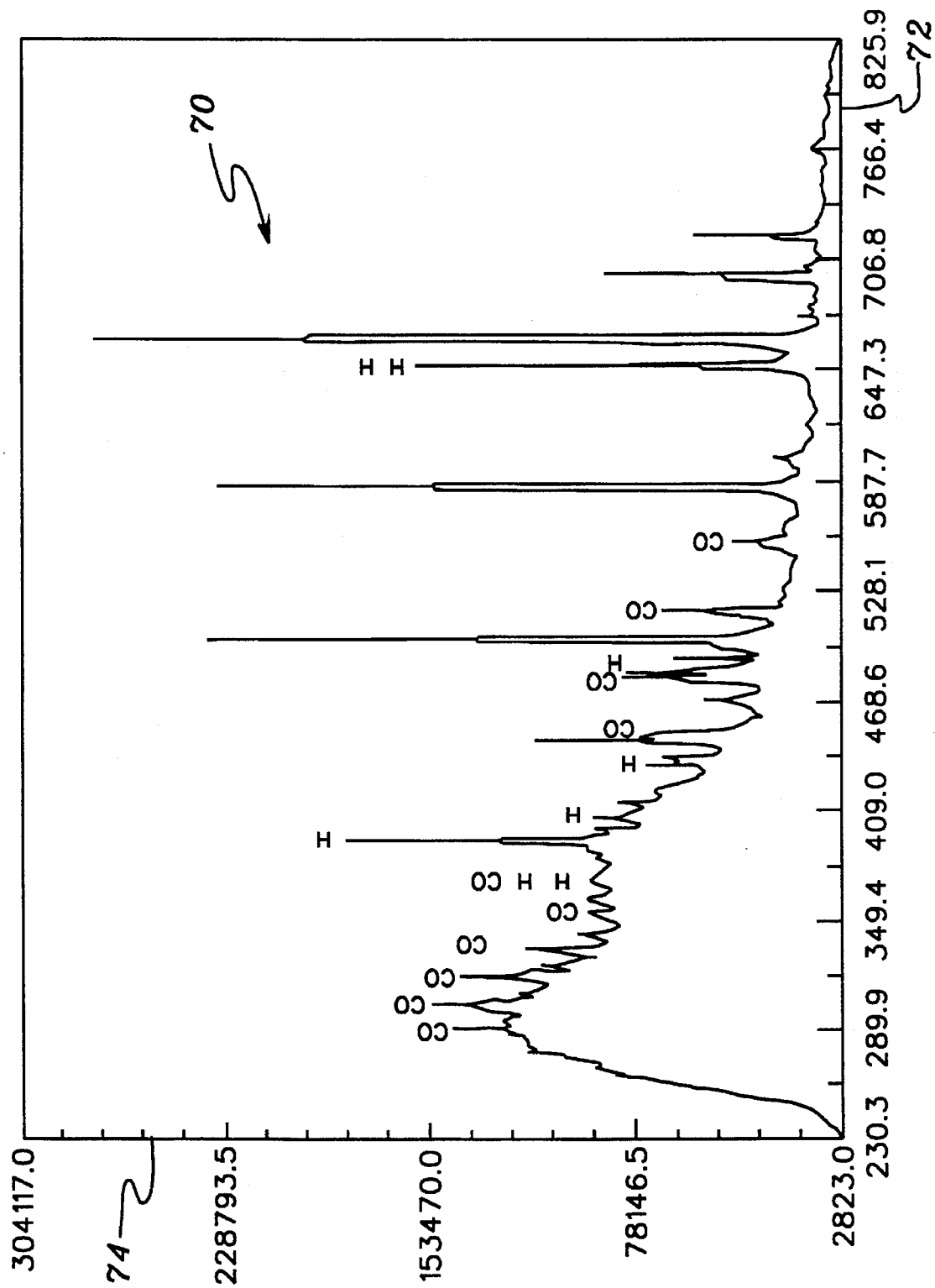
FIG. 11 depicts the plot of FIG. 10 with the results of selective identification of the gases indicated.

FIG. 10 depicts plot 70 without the results of the gas analysis and with prompt 86 requesting the user to indicate which gas or gases from a list of predetermined choices system 54 is to attempt to correlate to peaks in plot 70, that is, run the OES Impurity Analysis only for the indicated gases (hereinafter referred to as "selective identification"). In the exemplary embodiment herein described, prompt 86 requests the user to type a "y" next to each gas to be selectively identified. The result of running selective identification for the indicated gases in FIG. 10 is depicted in FIG. 11. Note that only those peaks associated with selectively identified gases, in this case, hydrogen and carbon monoxide, are labeled.

Figure 12:
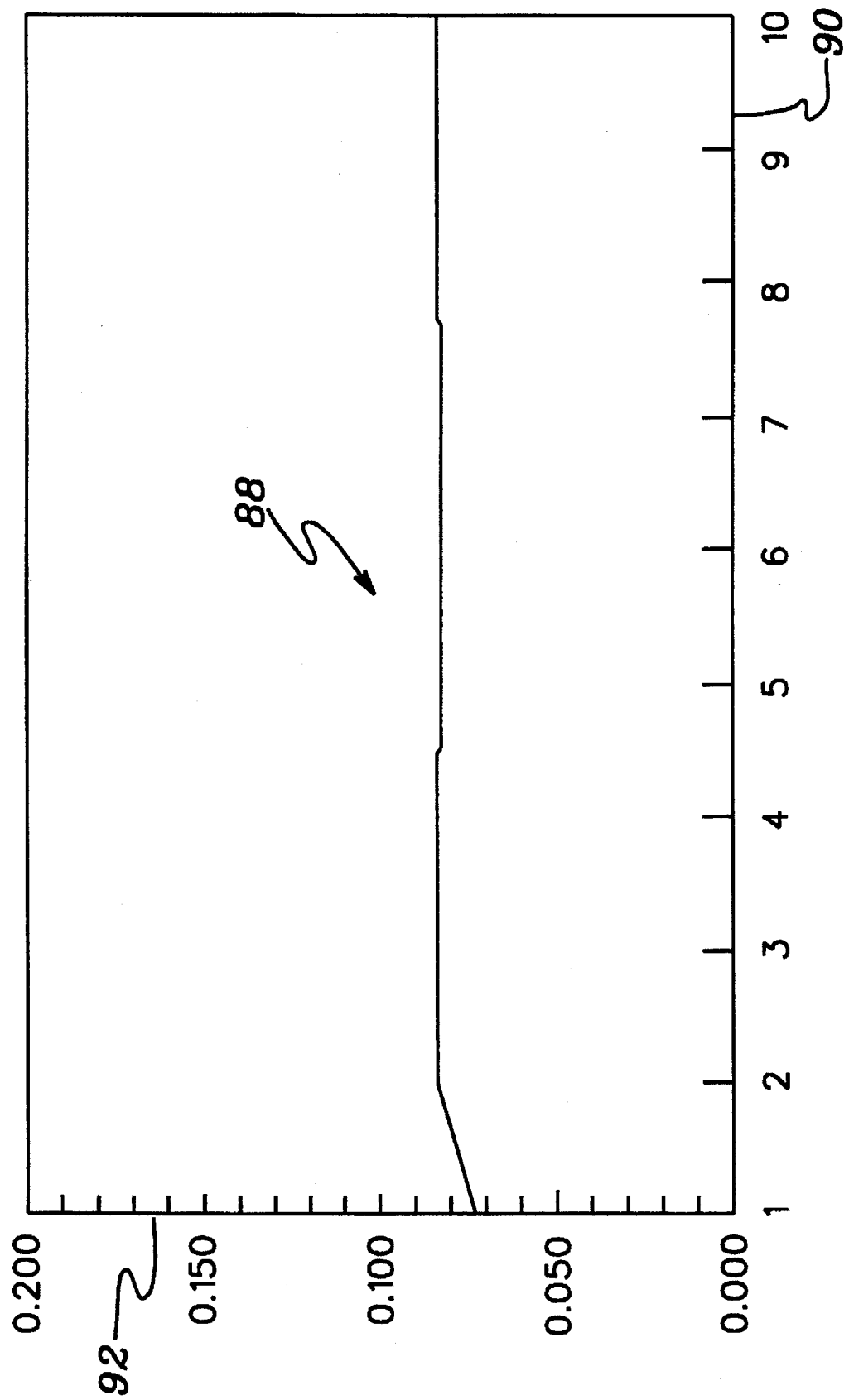
FIG. 12 depicts a plot of changes for a given gas over time, i.e., fingerprinting according to the present invention.

The present invention also allows for the display of the results of running OESIA to analyze each in a series of OES data taken with the same equipment over time to determine how the gaseous composition of the plasma changes over time (hereinafter referred to as "fingerprinting"). In practice, the user is capable of graphing a particular wavelength (or peak) over time, or graphing all wavelengths (or peaks) associated with a particular gas over time simply by indicating same to system 54. FIG. 12 depicts, in graphical form, the results of running the fingerprinting routine, discussed in more detail subsequently, on OES data taken at ten intervals for argon. Shown therein is plot 88 with time intervals on the X axis 90 plotted against an indicator of a change in relative intensity at a particular wavelength on the Y axis 92. Preferably, this indicator is a ratio of the relative intensity at that particular wavelength (or peak) to the sum of the relative intensities at peaks in a spectral plot (not shown) like that of plot 70 in FIG. 6.

Figure 13:
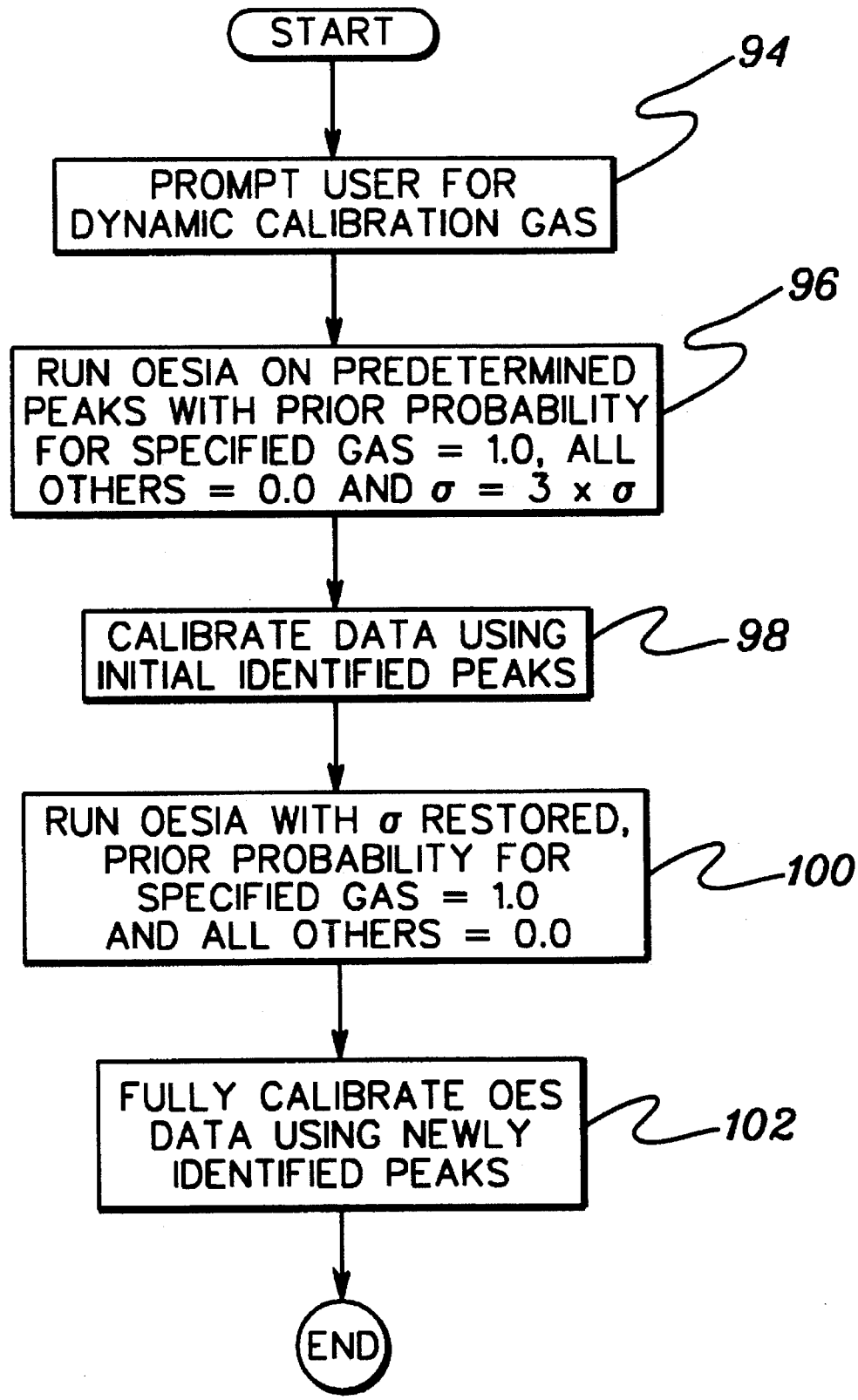
FIG. 13 is a flow diagram for dynamic calibration according to the present invention.

FIG. 13 is a flow diagram for the dynamic calibration routine referred to above. The user is first prompted in some fashion to identify the dynamic calibration gas, STEP 94 "PROMPT USER FOR DYNAMIC CALIBRATION GAS". The gas identification analysis (again, referred to herein as "OESIA") is then run with the prior probability for the specified gas set to 1.0, all other prior probabilities set to 0.0 and the value of σ (sigma) set to three times its normal value (say, 0.2) on a predetermined number of peaks in the graph, for example, five peaks, STEP 96 "RUN OESIA ON PREDETERMINED PEAKS WITH PRIOR PROBABILITY FOR SPECIFIED GAS=1.0, ALL OTHERS=0.0 AND σ=3×σ". Preferably, the predetermined peaks having the highest relative intensity are used. However, it will be understood that other criteria for which peaks to be used could be chosen, for example, the lowest peaks or a sampling of peaks from different areas of the graph.

Next, the OES data is initially calibrated using the predetermined number of identified peaks, STEP 98 "CALIBRATE DATA USING INITIAL IDENTIFIED PEAKS". To accomplish the calibration, the peaks are first assigned to values in existing OES peak charts for known gases listing a wavelength and corresponding relative intensity value for a particular gas. After assigning the peaks to known values in the OES peak chart, a scale can be determined providing the best "fit" for the OES data. Such a scale could be determined any number of ways, for example, through the use of linear regression. One skilled in the art will know how to determine the proper scaling, which may change in any given situation.

After calibrating the data on the first run, OESIA is run again for all of the peaks with σ restored to its original value (here, 0.2), the prior probability for the specified gas set to 1.0 and all other prior probabilities set to 0.0, STEP 100 "RUN OESIA WITH σ RESTORED, PRIOR PROBABILITY FOR SPECIFIED GAS=1.0 AND ALL OTHERS=0.0". Finally, the OES data is now fully calibrated using all of the newly identified peaks, STEP 102 "FULLY CALIBRATE OES DATA USING NEWLY IDENTIFIED PEAKS".

The operation of the learning routine referred to above will now be discussed in detail. In the following description, a known wavelength listed in an available table where an intensity peak occurs is designated by $w(1) \ldots w(m)$, where m is the total number of table entries associated with a given gas. Known relative intensity values listed in the table will be designated $f(1) \ldots f(m)$. Integer values referred to as numerators, $n(1) \ldots n(m)$, and denominators, $d(1) \ldots d(m)$ are initially set to zero (see FIG. 14, STEP 104 "$n(1) \ldots n(m)$ and $d(1) \ldots d(m)=0$"). The minimum wavelength in the raw OES data will be MIN and the maximum wavelength in the raw OES data will be MAX. Finally, $g(1) \ldots g(N)$ will be the set of different gaseous species present in the plasma process from which the OES data was obtained. In addition, the learning routine assumes that at least one of the peaks in a graph of the raw OES data have previously been associated with a gas, by, for example, a prior run of the OESIA or the user having manually identified it.

Figure 15:
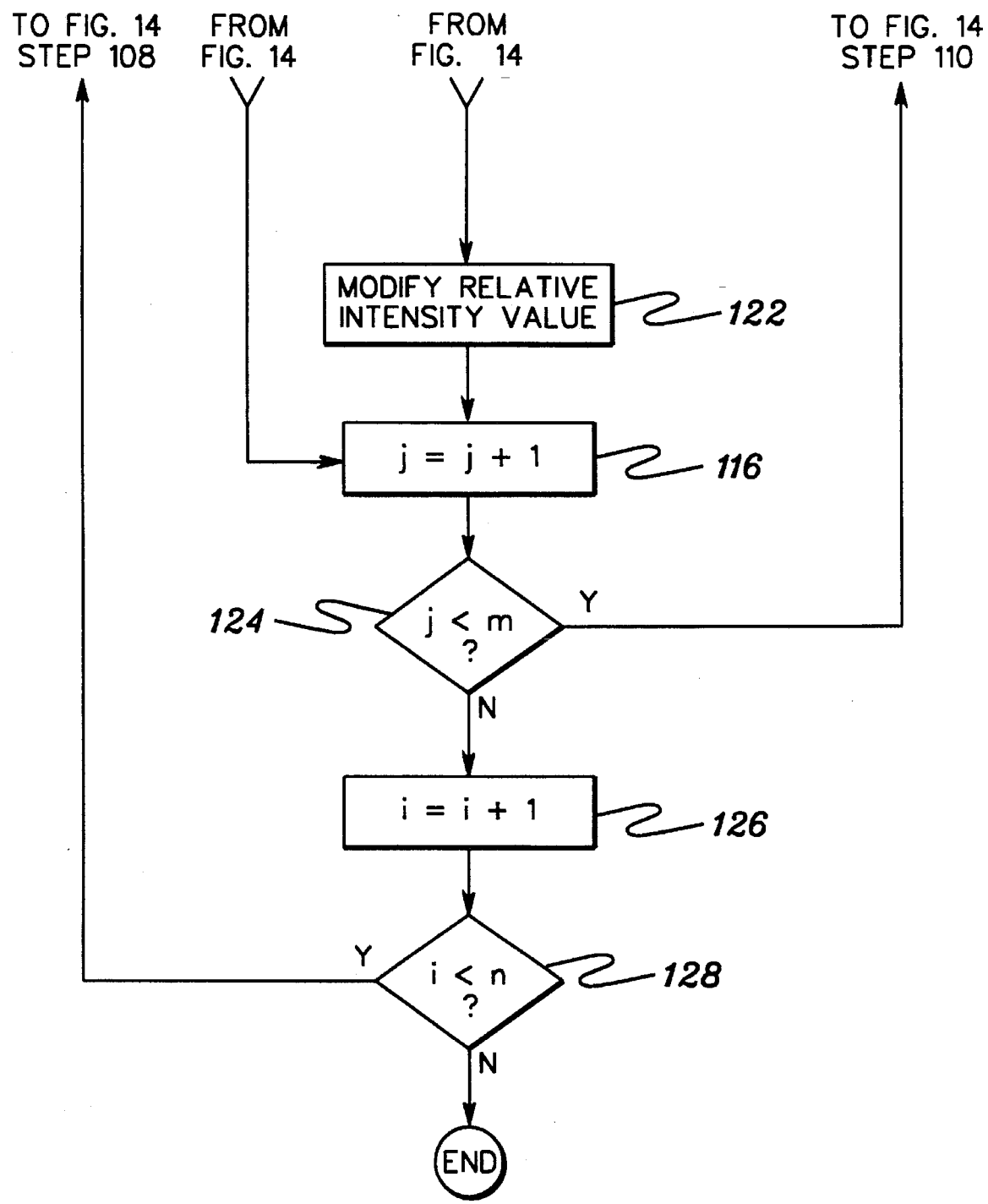

FIGS. 14 and 15 taken together are a flow diagram for the learning routine, the final output of which is the modifying of relative intensity values from the raw values obtained during the plasma process. Counters i and j are initialized to 1, STEP 106 "i=1" and STEP 108 "j=1". After initializing counters i and j, an inquiry is made as to whether the jth wavelength in the table is between MIN and MAX, INQUIRY 110 "w(j)>MIN AND w(j)<MAX?". If INQUIRY 110 is answered in the positive, denominator d(j) is incremented, STEP 112 "d(j)=d(j)+1". Incrementing d(j) means that there is at least a reasonable chance of encountering a peak in the graph of raw OES data associated with the jth table entry value. Next, an inquiry is made as to whether table entry j has previously been assigned to a peak in the graph, INQUIRY 114 "TABLE ENTRY J PREVIOUSLY ASSIGNED?". If either INQUIRY 110 or INQUIRY 114 are answered in the negative, the j counter is incremented, STEP 116 "j=j+1".

If INQUIRY 114 is answered in the positive, the jth numerator is incremented, STEP 118 "n(j)=n(j)+1". After incrementing the jth numerator, an inquiry is made as to whether the jth denominator has exceeded five, INQUIRY 120 "d(j)>5?". If INQUIRY 120 is answered in the negative, it means there is insufficient information to modify the jth relative intensity value and the routine proceeds to STEP 116. If INQUIRY 120 is answered in the positive, then the jth relative intensity value is modified, STEP 122 "MODIFY RELATIVE INTENSITY VALUE". The jth relative intensity value F(j) is preferably modified according to the following set of equations:

$$p1=n(j)/d(j);$$

$$p2=log_e((p1\times1.10825)/(1-p1)); \text{ and}$$

$$F(j)=(p2-0.5244)/0.018847.$$

After modifying the relative intensity value, STEP 116 is returned to, i.e., the j counter is incremented. After performance of STEP 116 for any reason, an inquiry is made as to whether the j counter is less than m, the total number of table entries associated with the present gas of interest, INQUIRY 124 "j<m?". If INQUIRY 124 is answered in the positive, the routine returns to INQUIRY 110. If INQUIRY 124 is answered in the negative, the i counter is incremented, STEP 126 "i=i+1". Incrementing the i counter changes the gas in question. After incrementing the i counter, an inquiry is made as to whether the i counter is less than the total number of gaseous species of interest, INQUIRY 78 "i<N?". If INQUIRY 128 is answered in the positive, the routine returns to STEP 108. Finally, if there are no more gas species of interest left, i.e., INQUIRY 128 is answered in the negative, the routine ends.

While several aspects of the present invention have been described and depicted herein, alternative aspects may be effected by those skilled in the art to accomplish the same objectives. For example, although the dynamic calibration routine described herein calibrates based on a single gaseous specie input by the user, the routine could be altered to accommodate multiple gaseous species. Accordingly, it is intended by the appended claims to cover all such alternative aspects as fall within the true spirit and scope of the invention.

We claim:

1. A method for analyzing data derived from a plasma including a plurality of gaseous species, said method comprising:

inputting said data into a computer;

indicating to said computer a gaseous specie to be assumed present in said plasma;

automatically calibrating via said computer said data based on said indicated gaseous specie; and identifying at least one of said plurality of gaseous species.

2. The method of claim 1 wherein said step of identifying is automatically performed by said computer in response to appropriate input.

3. The method of claim 1, wherein said computer includes a display, said method further comprising:

automatically displaying said data; and automatically displaying said automatically calibrated data.

4. The method of claim 3, wherein each of said data and said automatically calibrated data include relative intensity data and corresponding electromagnetic wavelength data and wherein each said step of automatically displaying comprises plotting said relative intensity data against said corresponding electromagnetic wavelength data.

5. The method of claim 4 wherein said step of automatically calibrating comprises creating a scale for said corresponding electromagnetic wavelength data.

6. The method of claim 5 wherein said step of creating comprises incorporating linear regression.

7. The method of claim 4, wherein said step of plotting comprises creating a plot and wherein said method further comprises creating an exploded view of a portion of said plot.

8. The method of claim 1 wherein said step of indicating comprises indicating to said computer said gaseous specie to be assumed present in response to a prompt therefor from said computer.

9. The method of claim 1, wherein said data includes relative intensity data and wherein said step of indicating comprises indicating to said computer a gaseous specie expected to have high relative intensity data in comparison to the other of said relative intensity data corresponding to the other of said plurality of gaseous species.

10. The method of claim 1, wherein said computer includes a memory storing known plasma data for a predetermined plurality of gaseous species and wherein said step of automatically calibrating comprises correlating said data to said known plasma data for said indicated gaseous specie.

11. The method of claim 10, wherein said data includes a plurality of sets of data and wherein said step of correlating comprises correlating a predetermined number of said plurality of sets of data to said known plasma data for said indicated gaseous specie.

12. The method of claim 2 wherein said step of identifying comprises automatically identifying via said computer said plurality of gaseous species.

13. The method of claim 12 further comprising automatically determining via said computer a configuration for said identified plurality of gaseous species.

14. The method of claim 13 further comprising automatically determining via said computer a probability that a given gaseous species in said configuration is actually present.

15. The method of claim 14 further comprising automatically determining via said computer a confidence interval for said probability.

16. The method of claim 1, wherein said data includes a plurality of sets of data and wherein said step of identifying comprises associating a predetermined number of peak sets of data with said at least one of said plurality of gaseous species.

17. The method of claim 1, wherein said data includes optical emission spectroscopy data, said optical emission spectroscopy data including relative intensity data and corresponding visible light wavelength data, and wherein said step of inputting said data comprises inputting said relative intensity data and said corresponding visible light wavelength data.

18. The method of claim 1 further comprising indicating to said computer at least one gaseous specie to be identified, wherein said step of identifying comprises automatically identifying via said computer said at least one gaseous specie.

19. The method of claim 18, wherein said step of automatically identifying comprises automatically identifying via said computer said at least one gaseous specie based on assumed parameters, said method further comprising modifying said assumed parameters based on results of said step of identifying such that a subsequent result of said step of automatically identifying is improved.

20. The method of claim 19, wherein said computer includes a memory storing for each of a predetermined plurality of gaseous species a plurality of sets of known plasma data, each of said plurality of sets of known plasma data including a known relative intensity value and a corresponding known electromagnetic wavelength, wherein said data includes a plurality of sets of data, each of said plurality of sets of data including a raw relative intensity value and a corresponding raw electromagnetic wavelength, and wherein said step of automatically identifying comprises:

(a) determining whether a given known electromagnetic wavelength is within a range of electromagnetic wavelengths present in said plurality of sets of data;

(b) modifying a relative probability that said given known electromagnetic wavelength will be present in said plurality of sets of data if said given known electromagnetic wavelength is determined in step (a) to be within said range, wherein said relative probability includes a numerator and a denominator;

(c) determining whether said given known electromagnetic wavelength has previously been associated with a given raw relative intensity value in said plurality of sets of data corresponding to said at least one gaseous specie to be identified if said relative probability has been modified in step (b);

(d) modifying said numerator if said given known electromagnetic wavelength is determined in step (c) to have previously been associated with said given raw relative intensity value;

(e) determining whether said denominator is greater than a predetermined number indicating insufficient information to modify a raw relative intensity value associated with said at least one gaseous specie to be identified; and (f) modifying said raw relative intensity value of step (e) if said denominator is determined in step (e) to be greater than said predetermined number.

21. The method of claim 20 wherein step (f) comprises modifying said raw relative intensity value F according to the following equation:

$$F=(p2-0.5244)/0.018847,$$

wherein $p2=\log_e ((p1 \times 1.10825)/(1-p1))$, $p1=n/d$, n=said numerator, and d=said denominator.

22. The method of claim 20 wherein said at least one gaseous specie to be identified includes at least two gaseous species, said method further comprising: (g) repeating steps (a) through (f) for each of said at least two gaseous species.

23. The method of claim 1 further comprising determining a change in a characteristic of said at least one of said plurality of gaseous species over time.

24. A method for identifying gaseous species in a plasma, comprising:

performing a plasma process, wherein a plasma comprising a plurality of gaseous species is created;

obtaining data from said plasma process;

inputting said data into a computer;

indicating to said computer a gaseous specie to be assumed present in said plurality of gaseous species;

automatically calibrating via said computer said data based on said indicated gaseous specie; and identifying at least one of said plurality of gaseous species.

25. The method of claim 24, wherein said plasma process is performed based on a plurality of plasma process parameters, said method further comprising:

altering at least one of said plasma process parameters based on said step of identifying; and performing said plasma process based on said altered at least one plasma process parameter.

26. The method of claim 24 further comprising indicating to said computer at least one gaseous species to be identified, wherein said step of identifying comprises identifying said at least one gaseous species.

27. The method of claim 26, wherein said step of identifying comprises identifying said at least one gaseous species based on assumed parameters, said method further comprising modifying said assumed parameters based on results of said step of identifying such that a subsequent result of said step of identifying is improved.

28. The method of claim 24 further comprising determining a change in a characteristic of said at least one of said plurality of gaseous species over time.

29. A system for assisting an analyst with analyzing data derived from a plasma including a plurality of gaseous species, said system comprising:

a computer;

means for inputting said data into said computer;

means for indicating to said computer a gaseous specie to be assumed present in said plurality of gaseous species;

means for automatically calibrating said data based on said indicated gaseous specie; and means for automatically identifying at least one of said plurality of gaseous species.

30. The system of claim 29 further comprising means for displaying said data and said calibrated data.

31. The system of claim 30 wherein said displaying means comprises means for graphically displaying said data and said calibrated data.

32. The system of claim 29 further comprising means for prompting said analyst for said gaseous specie to be assumed present.

33. The system of claim 29 further comprising a memory for storing known plasma data for a predetermined plurality of gaseous species.

34. The system of claim 33 wherein said automatic calibration means comprises means for correlating said data to said known plasma data.

35. The system of claim 34 further comprising means for determining a probability that a given identified gaseous specie is actually present.

36. The system of claim 29 wherein said automatic identification means comprises means for selectively identifying at least one gaseous specie.

37. The system of claim 36 further comprising means for improving automatic identification of said at least one gaseous specie based on past automatic identifications.

38. The system of claim 29 further comprising means for determining a change in a characteristic of said at least one of said plurality of gaseous species over time.

39. A method for analyzing data derived from a plasma including a plurality of gaseous species, said data including wavelength data and at least one data peak, said method comprising:

inputting said data into a computer;

indicating to said computer one of a gaseous specie and a wavelength to be associated with said at least one data peak;

automatically calibrating via said computer said data based on said indicated one of a gaseous specie and a wavelength; and identifying at least one of said plurality of gaseous species.

* * * * *

UNITED STATES PATENT AND TRADEMARK OFFICE
CERTIFICATE OF CORRECTION

PATENT NO. : 5,546,322
DATED      : Aug. 13, 1996
INVENTOR(S) : George G. Gifford et al.

It is certified that error appears in the above-identified patent and that said Letters Patent are hereby corrected as shown below:

Attorney, Agent, or Firm    "Cutter D. Lawrence" should be --Lawrence D. Cutter--.

Signed and Sealed this

Twenty-eighth Day of January, 1997

Attest:

BRUCE LEHMAN

*Attesting Officer*   *Commissioner of Patents and Trademarks*